(12) United States Patent
Wang et al.

(10) Patent No.: US 8,663,951 B2
(45) Date of Patent: *Mar. 4, 2014

(54) METHOD OF PRODUCING VIRUS-LIKE PARTICLES OF PICORNAVIRUS USING A SMALL-UBIQUITIN-RELATED FUSION PROTEIN EXPRESSION SYSTEM

(75) Inventors: Ting-Fang Wang, Taipei (TW); Shu-Mei Liang, Bethesda, MD (US)

(73) Assignee: Academia Sinica, Taipei (TW)

( * ) Notice: Subject to any disclaimer, the term of this patent is extended or adjusted under 35 U.S.C. 154(b) by 468 days.

This patent is subject to a terminal disclaimer.

(21) Appl. No.: 12/683,568

(22) Filed: Jan. 7, 2010

(65) Prior Publication Data

US 2010/0183649 A1    Jul. 22, 2010

Related U.S. Application Data

(60) Provisional application No. 61/143,455, filed on Jan. 9, 2009.

(51) Int. Cl.
*C12N 15/41* (2006.01)
*A61K 39/125* (2006.01)

(52) U.S. Cl.
USPC ...... 435/69.7; 435/71.1; 435/71.2; 424/216.1

(58) Field of Classification Search
None
See application file for complete search history.

(56) References Cited

U.S. PATENT DOCUMENTS

| | | | | |
|---|---|---|---|---|
| 6,261,765 B1 * | 7/2001 | McCarthy et al. | ............... | 435/5 |
| 6,872,551 B2 * | 3/2005 | Lima et al. | .................. | 435/69.7 |
| 8,034,910 B2 * | 10/2011 | Wang | .......................... | 536/23.1 |

OTHER PUBLICATIONS

Lewis et al., Journal of Virology, 1991, 65(12):6572-6580.*
Lee et al., Protein Science, Jul. 2008, 17:1241-1248.*
Mossessova et al., "Ulp1-SUMO Crystal Structure and Genetic Analysis Reveal Conserved Interactions and a Regulatory Element Essential for Cell Growth in Yeast", *Molecular Cell*, vol. 5, pp. 865-876 (2000).
Butt et al., "SUMO Fusion Technology for Difficult-to-Express Proteins", *Protein Expression and Purification 43*, 1-9, (2005).

* cited by examiner

*Primary Examiner* — Stacy B. Chen
(74) *Attorney, Agent, or Firm* — Cesari and McKenna, LLP (57) ABSTRACT

A method for producing picornaviral capsid protein complexes (e.g., picornavirus like particles) in *E. coli* using a small-ubiquitin-related fusion protein expression system and an *E. coli* strain used in practicing this method. Also disclosed is use of the picornaviral capsid protein complexes like thus prepared for eliciting immune responses.

20 Claims, 2 Drawing Sheets

SEQUENCE LISTING

<160> NUMBER OF SEQ ID NOS: 4

<210> SEQ ID NO 1
<211> LENGTH: 98
<212> TYPE: PRT
<213> ORGANISM: Saccharomyces cerevisiae

<400> SEQUENCE: 1

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

-continued

Phe Leu Tyr Asp Gly Ile Arg Ile Gln Ala Asp Gln Thr Pro Glu Asp
 65                  70                  75                  80

Leu Asp Met Glu Asp Asn Asp Ile Ile Glu Ala His Arg Glu Gln Ile
                 85                  90                  95

Gly Gly

<210> SEQ ID NO 2
<211> LENGTH: 287
<212> TYPE: PRT
<213> ORGANISM: Foot-and-mouth disease virus

<400> SEQUENCE: 2

Asn Thr Gly Ser Ile Ile Asn Asn Tyr Tyr Met Gln Gln Tyr Gln Asn
  1               5                  10                  15

Ser Met Asp Thr Gln Leu Gly Asp Asn Ala Ile Ser Gly Gly Ser Asn
                 20                  25                  30

Glu Gly Ser Thr Asp Thr Thr Ser Thr His Thr Asn Asn Thr Gln Asn
             35                  40                  45

Asn Asp Trp Phe Ser Lys Leu Ala Asn Thr Ala Phe Ser Gly Leu Phe
         50                  55                  60

Gly Ala Leu Leu Ala Asp Lys Lys Thr Glu Glu Thr Thr Leu Leu Glu
 65                  70                  75                  80

Asp Arg Ile Leu Thr Thr Arg Asn Gly His Thr Thr Ser Thr Thr Gln
                 85                  90                  95

Ser Ser Val Gly Val Thr Tyr Gly Tyr Ala Thr Ala Glu Asp Phe Val
            100                 105                 110

Ser Gly Pro Asn Thr Ser Gly Leu Glu Thr Arg Val Val Gln Ala Glu
        115                 120                 125

Arg Phe Phe Lys Thr His Leu Phe Asp Trp Val Thr Ser Asp Pro Phe
    130                 135                 140

Gly Arg Cys His Leu Leu Glu Leu Pro Thr Asp His Lys Gly Val Tyr
145                 150                 155                 160

Gly Ser Leu Thr Asp Ser Tyr Ala Tyr Met Arg Asn Gly Trp Asp Val
                165                 170                 175

Glu Val Thr Ala Val Gly Asn Gln Phe Asn Gly Gly Cys Leu Leu Val
            180                 185                 190

Ala Met Val Pro Glu Leu Arg Ser Ile Ser Lys Arg Glu Leu Tyr Gln
        195                 200                 205

Leu Thr Leu Phe Pro His Gln Phe Ile Asn Pro Arg Thr Asn Met Thr
    210                 215                 220

Ala His Ile Thr Val Pro Tyr Leu Gly Val Asn Arg Tyr Asp Gln Tyr
225                 230                 235                 240

Lys Val His Lys Pro Trp Thr Leu Val Val Met Val Ala Ala Pro Leu
                245                 250                 255

Thr Val Asn Asn Glu Gly Ala Pro Gln Ile Lys Val Tyr Ala Asn Ile
            260                 265                 270

Ala Pro Thr Asn Val His Val Ala Gly Glu Leu Pro Ser Lys Glu
        275                 280                 285

<210> SEQ ID NO 3
<211> LENGTH: 213
<212> TYPE: PRT
<213> ORGANISM: Foot-and-mouth disease virus

<400> SEQUENCE: 3

Thr Thr Ser Ala Gly Glu Ser Ala Asp Pro Val Thr Ala Thr Val Glu
  1               5                  10                  15

```
Asn Tyr Gly Gly Glu Thr Gln Val Gln Arg Arg Gln His Thr Asp Ile
            20                  25                  30

Ala Phe Ile Leu Asp Arg Phe Val Lys Val Lys Pro Lys Glu Gln Val
            35                  40                  45

Asn Val Leu Asp Leu Met Gln Ile Pro Ala His Thr Leu Val Gly Ala
50                      55                  60

Leu Leu Arg Thr Ala Thr Tyr Tyr Phe Ser Asp Leu Glu Leu Ala Val
65                  70                  75                  80

Lys His Glu Gly Asp Leu Thr Trp Val Pro Asn Gly Ala Pro Glu Thr
                85                  90                  95

Ala Leu Asp Asn Thr Thr Asn Pro Thr Ala Tyr His Lys Glu Pro Leu
            100                 105                 110

Thr Arg Leu Ala Leu Pro Tyr Thr Ala Pro His Arg Val Leu Ala Thr
            115                 120                 125

Val Tyr Asn Gly Ser Ser Lys Tyr Gly Asp Thr Ser Thr Asn Asn Val
            130                 135                 140

Arg Gly Asp Leu Gln Val Leu Ala Gln Lys Ala Glu Arg Thr Leu Pro
145                 150                 155                 160

Thr Ser Phe Asn Phe Gly Ala Ile Lys Ala Thr Arg Val Thr Glu Leu
                165                 170                 175

Leu Tyr Arg Met Lys Arg Ala Glu Thr Tyr Cys Pro Arg Pro Leu Leu
            180                 185                 190

Ala Ile Gln Pro Ser Asp Ala Arg His Lys Gln Arg Ile Val Ala Pro
            195                 200                 205

Ala Lys Gln Leu Leu
            210

<210> SEQ ID NO 4
<211> LENGTH: 220
<212> TYPE: PRT
<213> ORGANISM: Foot-and-mouth disease virus

<400> SEQUENCE: 4

Gly Ile Phe Pro Val Ala Cys Ser Asp Gly Tyr Gly Gly Leu Val Thr
1               5                   10                  15

Thr Asp Pro Lys Thr Ala Asp Pro Val Tyr Gly Lys Val Phe Asn Pro
            20                  25                  30

Pro Arg Asn Leu Leu Pro Gly Arg Phe Thr Asn Leu Leu Asp Val Ala
            35                  40                  45

Glu Ala Cys Pro Thr Phe Leu His Phe Asp Gly Asp Val Pro Tyr Val
50                  55                  60

Thr Thr Lys Thr Asp Ser Asp Arg Val Leu Ala Gln Phe Asp Leu Ser
65                  70                  75                  80

Leu Ala Ala Lys His Met Ser Asn Thr Phe Leu Ala Gly Leu Ala Gln
                85                  90                  95

Tyr Tyr Thr Gln Tyr Ser Gly Thr Ile Asn Leu His Phe Met Phe Thr
            100                 105                 110

Gly Pro Thr Asp Ala Lys Ala Arg Tyr Met Val Ala Tyr Ala Pro Pro
            115                 120                 125

Gly Met Glu Pro Pro Lys Thr Pro Glu Ala Ala Ala His Cys Ile His
            130                 135                 140

Ala Glu Trp Asp Thr Gly Leu Asn Ser Lys Phe Thr Phe Ser Ile Pro
145                 150                 155                 160

Tyr Leu Ser Ala Ala Asp Tyr Ala Tyr Thr Ala Ser Asp Val Ala Glu
                165                 170                 175
```

-continued

```
Thr Thr Asn Val Gln Gly Trp Val Cys Leu Phe Gln Ile Thr His Gly
            180                 185                 190

Lys Ala Asp Gly Asp Ala Leu Val Val Leu Ala Ser Ala Gly Lys Asp
        195                 200                 205

Phe Asp Leu Arg Leu Pro Val Asp Ala Arg Thr Gln
    210                 215                 220
```

METHOD OF PRODUCING VIRUS-LIKE PARTICLES OF PICORNAVIRUS USING A SMALL-UBIQUITIN-RELATED FUSION PROTEIN EXPRESSION SYSTEM

RELATED APPLICATION

This application claims priority to U.S. Provisional Application No. 61/143,455, filed on Jan. 9, 2009, the content of which is hereby incorporated by reference in its entirety.

BACKGROUND OF THE INVENTION

Virus-like particles (VLPs), formed by self-assembly of viral envelop or capsid proteins, resemble viruses, from which the envelop/capsid proteins derive, but lack viral nucleic acids. Like viruses, they are highly immunogenic; unlike viruses, they are not infectious. Given these two features, VLPs are excellent vaccine candidates. They also have the potential for use in drug delivery due to their capacity to encapsulate a drug during assembly.

VLPs can be prepared by conventional recombinant technology. More specifically, one can express viral envelop/capsid proteins in a cell and then assemble the proteins to form particles. E. coli is commonly used as a host for expressing recombinant proteins. However, they are not suitable for producing VLPs as envelop/capsid proteins expressed therein are usually water insoluble.

SUMMARY OF THE INVENTION

The present invention is based on three unexpected discoveries: (1) co-expression in E. coli of foot-and-mouth disease virus (FMDV) capsid proteins VP0, VP1, and VP3, each fused with a Smt3 protein, yields a ternary protein complex composed of the three fusion proteins, (2) this ternary protein complex is converted to a FMDV-like particle upon U1P1 protease treatment, and (3) the FMDV-like particle elicits anti-FMDV immune responses in guinea pigs.

Accordingly, one aspect of this invention relates to an E. coli strain containing a plurality of nucleotide sequences. Each of the nucleotide sequences, operably linked to a promoter, contains a first fragment that encodes a Smt3 protein and a second fragment that encodes a capsid protein of a picornavirus (e.g., a FMDV). The second fragments in all of the nucleotide sequences, taken together, encode all of the capsid proteins for a virus-like particle of the picornavirus. In one or more of the nucleotide sequences, the first and second fragments are linked via an SfoI restriction site. At least one of the nucleotide sequence can further contain a third fragment that encodes a protein tag (e.g., hexa-His, maltose binding protein, N-utilizing substance A, thioredoxin, calmodulin-binding protein, glutathione S-transferase, or α-factor). This third fragment preferably is located upstream to the first fragment in the same nucleotide sequence. In one example, the E. coli strain described above contains three nucleotide sequences, in which the second fragments encode FMDV capsid proteins VP0, VP1, and VP3.

Another aspect of this invention features a method of making a picornaviral capsid protein complex (e.g., a picornavirus-like particle) using the E. coli strain described above. This method includes (i) providing the E. coli strain, (ii) culturing it under conditions suitable for expression of fusion proteins, each containing Smt3 and one of the capsid proteins, and for formation of a capsid protein complex composed of the fusion proteins, (iii) collecting cells of the E. coli strain for isolation of the capsid protein complex, and optionally (iv) converting the protein complex thus isolated to a picornavirus-like particle by an U1P1 protease. The converting step can be performed in the presence of a therapeutic agent so that the agent is encapsulated in the resultant picornavirus-like particle.

In yet another aspect, this invention features a method for eliciting an immune response against a FMDV by administering to a subject in need thereof (e.g., a cloven-hoofed animal) an effective amount of a FMDV-like particle, which can include capsid proteins VP0, VP1, and VP3.

Also within the scope of this invention is use of a FMDV-like particle mentioned above in manufacturing a medicament for eliciting immune responses in a subject (e.g., a human).

The details of one or more embodiments of the invention are set forth in the description below. Other features or advantages of the present invention will be apparent from the following drawing and detailed description of several examples and also from the appended claims.

DETAILED DESCRIPTION OF THE INVENTION

Disclosed herein is a method of preparing a capsid protein complex of a picornavirus by co-expressing in E. coli necessary capsid proteins of that picornavirus using a small-ubiquitin-related modifier (SUMO) fusion protein expression system as described in Lee et al., Protein Sci. 17:1241-1248 (2008) and in U.S. Patent Applications Nos. 61/050,663 and 61/050,665. The term "capsid protein complex of a picornavirus" or "picornaviral capsid protein complex" refers to a protein complex formed by association of picornaviral capsid proteins necessary for viral particle assembly. This complex can be a VLP of a picornavirus.

To perform the method of this invention, multiple nucleotide sequences, either in one expression cassette or in multiple expression cassettes, can be constructed via conventional recombinant technology. An "expression cassette" is a nucleotide sequence designed for expressing one or more polypeptides of interest in host cells (e.g., E. coli cells). An expression cassette designed for expressing one or more polypeptides of interest in E. coli cells can include an E. coli promoter operably linked to one or more sequences encoding the one or more polypeptides. An "E. coli promoter" is a nucleotide sequence containing elements that initiate the transcription of an operably linked nucleic acid sequence in E. coli cells. At a minimum, a promoter contains an RNA polymerase binding site. It can further contain one or more enhancer elements which, by definition, enhance transcription, or one or more regulatory elements that control the on/off status of the promoter. Examples of E. coli promoter include, but are not limited to, the β-lactamase and lactose promoter systems (see Chang et al., Nature 275:615-624, 1978), the SP6, T3, T5, and T7 RNA polymerase promoters (Studier et al., Meth. Enzymol. 185:60-89, 1990), the lambda promoter (Elvin et al., Gene 87:123-126, 1990), the trp promoter (Nichols and Yanofsky, Meth. in Enzymology 101:155-164, 1983), and the Tac and Trc promoters (Russell et al., Gene 20:231-243, 1982).

Each of the nucleotide sequences mentioned above contains a fragment encoding a Smt3 protein, a fragment encoding a picornaviral capsid protein, and optionally, a fragment encoding a protein tag. These nucleotide sequences, taken together, are capable of expressing all of the capsid proteins, fused with the Smt3 protein and optionally the protein tag, that are necessary for forming a VLP of the picornavirus, from which the capsid proteins are derived. In one example, the nucleotide sequence encoding the Smt3 protein is upstream to the nucleotide sequence encoding the capsid protein and the two sequences are linked via a SfoI restriction site, i.e.,

```
5' . . . GGC▼GCC . . . 3'

3' . . . CCG▲CGG . . . 5',
``` coding for Gly-Gly.

The Smt3 protein can be the *Saccharomyces cerevisiae* Smt3 protein, the amino acid sequence of which is shown below:

```
Amino acid sequence of Saccharomyces cerevisiae
Smt3
                                         (SEQ ID NO: 1)
MSDSEVNQEAKPEVKPEVKPETHINLKVSDGSSEIFFKIKKTTPLRRLME

AFAKRQGKEMDSLRFLYDGIRIQADQTPEDLDMEDNDIIEAHREQIGG
```

It can also be a functional variant of this yeast Smt3, which is a polypeptide that shares a high sequence homology with Smt3 (i.e., having a sequence identity any percentage from 85% to 100%, such as at least 90%, 95%, 98%, or 99%) and possesses the function of yeast Smt3. When fused with a picornavirus capsid protein, the Smt3 protein can be cleaved by an Ulp1 protease to generate a free Smt3 protein having -Gly-Gly (encoded by the SfoI restriction site) at its C-terminus. See Mossessova et al., Mol. Cell 5:865-876 (2000). "U1p1 protease" is a polypeptide having the protease activity of *Saccharomyces cerevisiae* U1p1 protease. It can be a full-length *Saccharomyces cerevisiae* U1p1 protease or a fragment thereof (e.g., residues 403-621) that possesses the protease activity, or a fusion protein containing the full-length or a fragment thereof, and a protein tag (e.g., a $His_6$-tag).

The "percent identity" of two amino acid sequences is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

The picornaviral capsid proteins described herein can be naturally occurring capsid proteins of a picornavirus or their functional variants, i.e., having a sequence identity greater than 85% (e.g., 90%, 95%, or 99%) to their naturally occurring counterparts and possessing the same function of forming the shell of a picornaviral particle. Examples of picornaviruses are listed in Table 1 below:

TABLE 1

Representative Genus and Species of Picornavirus

| Genus | Species |
|---|---|
| Enterovirus | Bovine enterovirus |
| | Human enterovirus A |
| | Human enterovirus B |
| | Human enterovirus C |
| | Human enterovirus D |
| | Poliovirus |
| | Porcine enterovirus A |
| | Porcine enterovirus B |
| | Simian enterovirus A |
| Rhinovirus | Human rhinovirus A |
| | Human rhinovirus B |
| Hepatovirus (also classed as Heparnavirus | Hepatitis A virus |
| | Avian encephalomyelitis-like viruses |
| Cardiovirus | Encephalomyocarditis virus |
| | Theilovirus |
| Aphthovirus | Foot-and-mouth disease virus |
| | Equine rhinitis A virus |
| Parechovirus | Human parechovirus |
| | Ljungan virus |
| Erbovirus | Equine rhinitis B virus |
| Kobuvirus | Aichi virus |
| | Bovine kobuvirus |
| Teschovirus | Porcine teschovirus |

Picornavirus also includes hand foot and mouth disease virus, e.g., types A16 A4, A5, A7, A9, and A10 of Coxsackie A virus.

The multiple nucleotide sequences, included in one or more expression plasmids, are introduced into an *E. coli* host cell for expression of the Smt3-capsid fusion proteins, which form a complex in the *E. coli* cell. The complex can be isolated from the host cell and treated with U1P1 protease to release free capsid proteins. When the nucleotide sequences coding for Smt3 and for a capsid protein are linked via an SfoI site, U1P1 protease digestion yields a free capsid protein with no extra amino acid residues derived from a restriction site. The free capsid proteins released from U1P1 protease treatment self-assemble into VLPs.

These VLPs can be used as vaccines for inducing immune responses against the picornavirus that the VLPs resemble. To achieve this goal, a VLP of a picornavirus can be mixed with a pharmaceutically acceptable carrier (e.g., a phosphate buffered saline, a bicarbonate solution, or an adjuvant) to form a pharmaceutical composition and an effective amount of the pharmaceutical composition can be administered to a subject who suffers from or is at risk for infection with that picornavirus. In one example, the pharmaceutical composition contains a VLP that resembles a foot-and-mouth disease virus and is used to reduce the risk of developing foot-and-mouth disease in a cloven-hoofed animal (e.g., cattle, water buffalo, sheep, goats and pigs). In another example, the pharmaceutical composition contains a VLP that resembles a picornavirus capable of causing infections in humans (e.g., the human viruses listed in Table 1 above) and is used to reduce the risk of such human infections.

A pharmaceutically acceptable carrier is a carrier that is compatible with the active ingredient of the composition, and preferably, capable of stabilizing the active ingredient and not deleterious to the subject to be treated. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

To make the pharmaceutical composition mentioned above, the carrier can be selected on the basis of the mode and route of administration, and standard pharmaceutical practice. Suitable pharmaceutical carriers, as well as pharmaceutical necessities for their use, are described in Remington's Pharmaceutical Sciences. The carrier can also be an adjuvant, e.g., a cholera toxin, *Escherichia coli* heat-labile enterotoxin (LT), liposome, immune-stimulating complex (ISCOM), or immunostimulatory sequences oligodeoxynucleotides (ISS-ODN). In addition to the carrier, the pharmaceutical composition can also include a polymer that facilitates in vivo delivery. See Audran R. et al. Vaccine 21:1250-5, 2003; and Denis-Mize et al. Cell Immunol., 225:12-20, 2003.

Methods for preparing vaccines are generally well known in the art, as exemplified by U.S. Pat. Nos. 4,601,903; 4,599,231; 4,599,230; and 4,596,792. Vaccines may be prepared as injectables, as liquid solutions or emulsions. The VLPs described herein may be mixed with physiologically acceptable and excipients compatible. Excipients may include, water, saline, dextrose, glycerol, ethanol, and combinations thereof. The vaccine may further contain minor amounts of auxiliary substances such as wetting or emulsifying agents, pH buffering agents, or an adjuvant to enhance the effectiveness of the vaccines. Methods of achieving adjuvant effect for the vaccine includes use of agents, such as aluminum hydroxide or phosphate (alum), commonly used as 0.05 to 0.1 percent solutions in phosphate buffered saline. Vaccines may be administered parenterally, by injection subcutaneously or intramuscularly. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10-95% of the immunopeptide described herein.

The VLP-containing pharmaceutical composition described above is administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

The VLPs can also be used as vehicles for delivering therapeutic or diagnostic agents (e.g., an anti-cancer drug or an imaging molecule), which can be coated on the surface of a nano-particle (e.g., a magnetic bead and a quantum dot). More specifically, during their self-assembly, capsid proteins can pack therapeutic agents into the VLPs they formed. Thus, when performing the U1P1 protease treatment in the presence of a therapeutic agent, the free capsid proteins released from the protease digestion encapsulate the therapeutic agent while self-assembling into VLPs. The resultant VLPs facilitate in vivo delivery of the therapeutic agent when administered to a subject in need via a conventional route.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

Example 1

Preparation of Protein Complex Containing
His$_6$-Smt3-VP0, His$_6$-Smt3-VP1, and
His$_6$-Smt3-VP3 Fusion Proteins cDNAs encoding FMDV VP0, VP1, and VP3 were amplified by the sticky-end polymerase chain reaction cloning method described in Shih et al. Protein Sci. 11:1714-1719 (2002). The amino acid sequences of the three FMDV capsid proteins are shown below:

```
Amino acid sequence of FMDV capsid protein VP0
                                        (SEQ ID NO: 2)
N T G S I I N N Y Y M Q Q Y Q N S M D T Q L G D N

A I S G G S N E G S T D T T S T H T N N T Q N N D

W F S K L A N T A F S G L F G A L L A D K K T E E

T T L L E D R I L T T R N G H T T S T T Q S S V G

V T Y G Y A T A E D F V S G P N T S G L E T R V V

Q A E R F F K T H L F D W V T S D P F G R C H L L

E L P T D H K G V Y G S L T D S Y A Y M R N G W D

V E V T A V G N Q F N G G C L L V A M V P E L R S

I S K R E L Y Q L T L F P H Q F I N P R T N M T A

H I T V P Y L G V N R Y D Q Y K V H K P W T L V V

M V A A P L T V N N E G A P Q I K V Y A N I A P T

N V H V A G E L P S K E

Amino acid sequence of FMDV capsid protein VP1
                                        (SEQ ID NO: 3)
T T S A G E S A D P V T A T V E N Y G G E T Q V Q

R R Q H T D I A F I L D R F V K V K P K E Q V N V

L D L M Q I P A H T L V G A L L R T A T Y Y F S D

L E L A V K H E G D L T W V P N G A P E T A L D N

T T N P T A Y H K E P L T R L A L P Y T A P H R V

L A T V Y N G S S K Y G D T S T N N V R G D L Q V

L A Q K A E R T L P T S F N F G A I K A T R V T E

L L Y R M K R A E T Y C P R P L L A I Q P S D A R

H K Q R I V A P A K Q L L

Amino acid sequence of FMDV capsid protein VP3
                                        (SEQ ID NO: 4)
G I F P V A C S D G Y G G L V T T D P K T A D P V

Y G K V F N P P R N L L P G R F T N L L D V A E A

C P T F L H F D G D V P Y V T T K T D S D R V L A

Q F D L S L A A K H M S N T F L A G L A Q Y Y T Q
```

-continued

```
Y S G T I N L H F M F T G P T D A K A R Y M V A Y

A P P G M E P P K T P E A A A H C I H A E W D T G

L N S K F T F S I P Y L S A A D Y A Y T A S D V A

E T T N V Q G W V C L F Q I T H G K A D G D A L V

Figure 1:
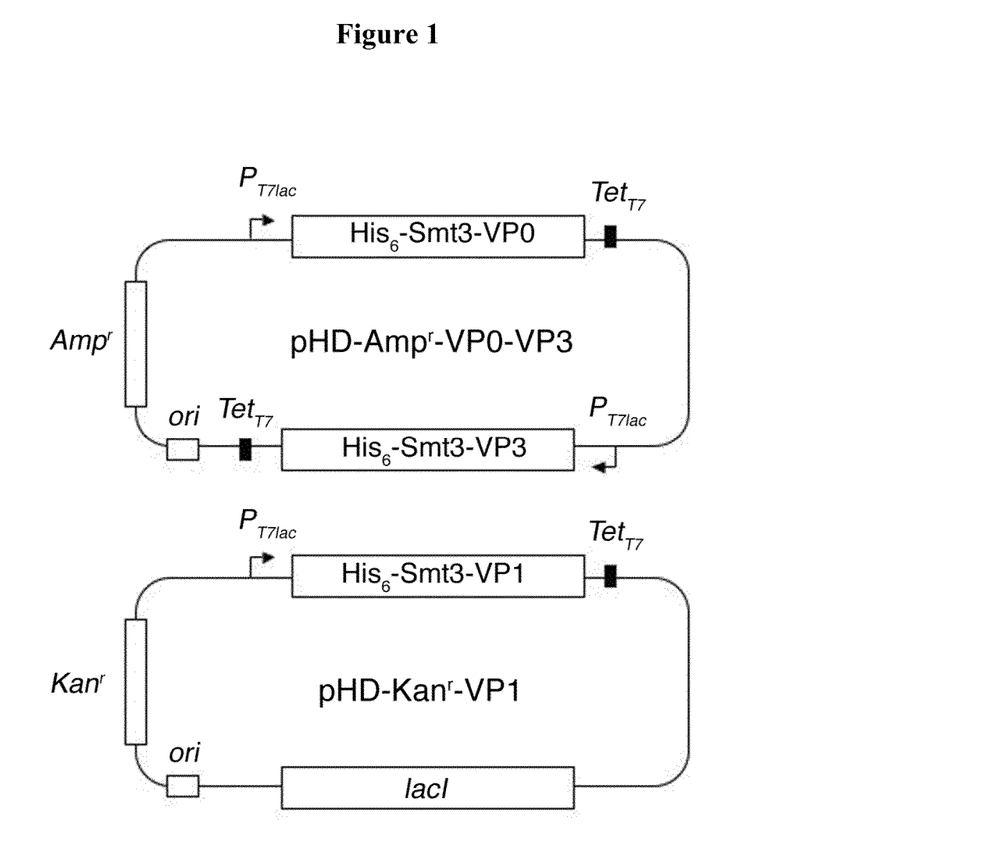
FIG. 1 is a diagram showing expression constructs for producing $His_6$-Smt3-VP0, $His_6$-Smt3-VP1, and $His_6$-Smt3-VP3 fusion proteins.

V L A S A G K D F D L R L P V D A R T Q
``` cDNAs encoding VP0 and VP1 were cloned into expression vector pHD-Kan$^r$ via cloning sites SfoI and XhoI to produce expression plasmids pHD-Kan$^r$-VP0 and pHD-Kan$^r$-VP1; the cDNA encoding VP3 was cloned into expression vectors pHD-Amp$^r$ via the same cloning site to produce expression plasmid pHD-Amp$^r$-VP3. Expression vectors pHD-Amp$^r$ and pHD-Kan$^r$ each include a T7 lac promoter ($P_{T7lac}$), a T7 terminator ($Tet_{T7}$), a nucleotide sequence encoding a hexa-His tag, and a nucleotide sequence encoding Smt3. See Lee et al., Protein Sci. 17:1241-1248 (2008). A DNA fragment containing $P_{T7lac}$, His$_6$-Smt3-VP0, and $Tet_{T7}$ was PCR amplified from the pHD-Kan$^r$-VP0 plasmid and then subcloned into pHD-Amp$^r$-VP3 construct to produce expression plasmid pHD-Amp$^r$-VP0-VP3, which expresses both His$_6$-Smt3-VP0 and His$_6$-Smt3-VP3 fusion proteins. See FIG. 1.

Expression plasmids pHD-Amp$^r$-VP0-VP3 and pHD-Kan$^r$-VP1 were introduced into the BL21(DE3)-RIL E. coli cell (Stratagen, USA) and positive transformants were isolated by ampicillin and kanamycin selection. A transformant containing both pHD-Amp$^r$-VP0-VP3 and pHD-Kan$^r$-VP1 was cultured overnight at 37° C. in the presence of 100 mg/L ampicillin and 300 mg/L kanamycin to produce overnight cultures. The overnight culture was then transferred to 1 L fresh Luria-Bertani medium, grew at 37° C. until they reached an $OD_{600}$ value of about 0.5-0.6. Isopropyl β-D-1-thiogalactopyranoside (1 mM) was then added to the culture to induce protein expression. The induced cells were grown at 20° C. for 12 h, harvested, and then centrifuged at 9,000×g for 30 min. The cell pellet was lyzed according to the method described in Wang et al., J. Biol. Chem 268:26049-26051 (1993), except that a different lysis buffer [50 mM Tris-HCl (pH 7.4), 300 mM NaCl, 0.2 mM EGTA (pH 8.0)] was used here to prevent non-specific association of His$_6$-Smt3-VP0, His$_6$-Smt3-VP1 or His$_6$-Smt3-VP3 with bacterial DNA. After centrifugation, the soluble fraction was mixed with 2 mL of $Ni^{2+}$ resins (Amersham, USA) to which the His$_6$-Smt3-VP0, His$_6$-Smt3-VP1, and His$_6$-Smt3-VP3 fusion proteins bind. The $Ni^{2+}$ resins were washed three times with 30 mL of wash buffer [50 mM Tris-HCl (pH 7.4), 300 mM NaCl, 0.2 mM EGTA (pH 8.0), 40 mM imidazole (pH 8.0)] and the fusion proteins bound to them were then eluted.

The eluted fraction was subjected to SDS-PAGE analysis to determine protein purity. Upon Coomassie Blue staining, three protein bands were observed on the gel. These proteins have molecular weights close to the theoretical molecular weights of fusion proteins His$_6$-Smt3-VP0, His$_6$-Smt3-VP1, and His$_6$-Smt3-VP3, i.e., 45,175 Da, 37,057 Da and 37,245 Da, respectively.

High-pressure liquid chromatography (HPLC) was employed to determine the molecule weight of the fusion proteins (non-denatured) contained in the eluted fraction.

Figure 2:
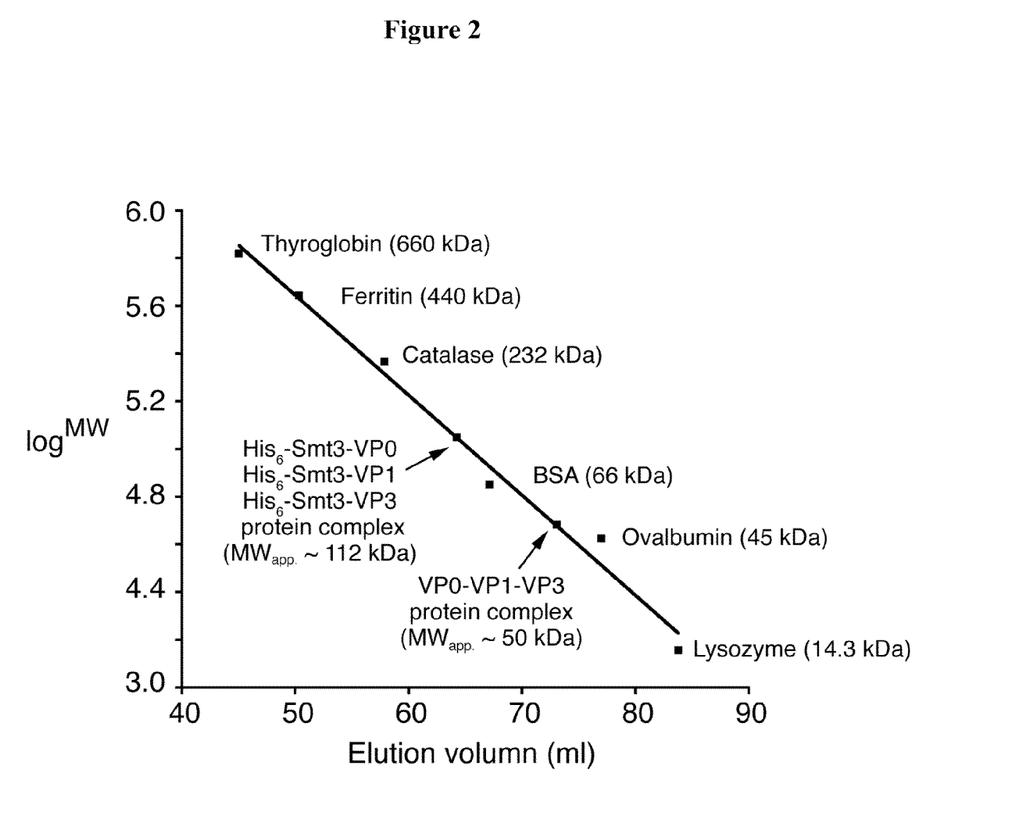
FIG. 2 is a diagram showing a molecular weight calibration curve and the molecular weights of the $His_6$-Smt3-VP0/$His_6$-Smt3-VP1/$His_6$-Smt3-VP3 and VP0/VP1/VP3 complexes determined accordingly.

First, a calibration curve of Molecular weight vs. Elution volume was generated using a molecular mass standard including thyroglobulin, ferritin, catalase, bovine serum albumin, ovalbumin and lysozyme; supplied by GE healthcares. The standard was loaded onto a HiLoad 16/60 Superdex column (GE Healthcare) and eluted with an elution buffer containing 50 mM Tris-HCl (pH 7.4), 300 mM NaCl, and 0.2 mM EGTA (pH 8.0) at a flow rate of 1.0 ml/min. The eluted fractions were measured continuously for their optical densities at 280 nm. The average elution volume (Kay) of each protein component in the standard was calculated as follows: $Kav=(Ve-V_0)/(Vt-V_0)$, where Ve and Vt represent elution volume of the protein component and DTT, respectively, and $V_0$ (void volume) was determined using blue dextran 2000 (GE, Healthcare). A calibration curve was produced based on the average elution volume of each protein component in the standard versus its molecular weight. See FIG. 2.

Next, the eluted fraction containing the fusion proteins His$_6$-Smt3-VP0, His$_6$-Smt3-VP1, and His$_6$-Smt3-VP3 was loaded onto the same HiLoad 16/60 Superdex column and eluted using the same elution buffer at the same flow rate noted above. Its average elution volume was calculated following the formula also described above. Based on the average elution volume, the molecular weight(s) of the protein component(s) contained in the eluted fraction was determined in view of the calibration curve. The result thus obtained indicates that the eluted fraction contained a single protein component having the molecular weight of ~112 kDa. See FIG. 1, panel b. This date shows that the fusion proteins His$_6$-Smt3-VP0, His$_6$-Smt3-VP1, and His$_6$-Smt3-VP3 form a ternary protein complex at the ratio of 1:1:1.

Example 2

Preparation of FMDV-Like Particles

The His$_6$-Smt3-VP0/His$_6$-Smt3-VP1/His$_6$-Smt3-VP3 ternary protein complex described in Example 1 above was treated with U1P1 protease to remove the His$_6$-Smt3 moiety, following the procedures described in Lee et al., Protein Sci. 17:1241-1248 (2008). SDS-PAGE analysis showed that the protease-digested product contains three proteins having molecular weights ~32 kDa, 29 kDa and 26 kDa, which correspond to the theoretical molecular weights of VP0, VP3, and VP1, respectively. An Edman degradation assay was then performed to determine the N-termini amino acid residues of these three proteins. Results thus obtained showed that they were identical to the N-termini amino acid residues of VP0, VP1, and VP3. It confirms that the proteins contained in the protease-digested products were indeed FMDV capsid proteins VP0, VP1, and VP3.

The protease-treated product was then subjected to the HPLC assay described above. The results showed that VP0, VP1, and VP3 contained in this product formed a complex at a ratio of 1:1:1. This complex was analyzed by electron microscopy as follows.

A droplet (4 μl) of a sample containing the protease-digested product was placed on a copper grid (300 mesh, Pelco, USA) coated with fresh carbon for 1 min at room temperature. Any excess fluid was carefully removed from the edge of the grid using a Whatman #1 filter paper (Whatman Inc., USA). The sample was then stained with 2.5% uranyl acetate for 4 min and excess fluid was removed afterwards. The stained sample was air dried at room temperature and then subjected to analysis using Bio-transmission electron microscopy (EM), using a Tecnai G2 Spirit Bio TWIN (FEI Co., Netherlands) at an acceleration voltage of 120 kV. Images were recorded using a slowscan CCD camera (Gatan Multi-Scan 600) at a resolution of at least 1024×1024 pixels.

Results thus obtained showed that the protease-digested product contains round-shaped particles having an average diameter of around 25 nm. This diameter is very close to the average diameter of FMDV viral particles, i.e., 27 nm (see Grubman et al., Clin Microbiol Rev. 17:465-493 (2004). These results indicate that U1P1 protease treatment converted the His$_6$-Smt3-VP0/His$_6$-Smt3-VP1/His$_6$-Smt3-VP3 ternary protein complex to virus-like particles containing FMDV capsid proteins VP0, VP1, and VP3.

Example 3

Immune Responses Elicited by FMDV-Like Particles

The VLPs of FMDV prepared by the method described in Example 2 above was examined as follows to determine their activity in inducing immune responses.

First, HEK293 cells, transfected with p5×NFκB-Luc, EGFP-N1 (as a control plasmid), pcDNA3.1-TLR2, or pcDNA3.1 (as a blank control), were treated with (a) 1 μm Pam3csk4 (a TLR2 ligand; a positive control), (b) Tris buffer (20 mM Tris-Cl, pH 8.0, and 100 mM NaCl; a blank control), (c) 90 μg/ml BEI-inactivated FMDV (a positive control), and (d) VLPs at various doses (i.e., 0.6, 1, and 3 μg/ml). Twenty-four hours after treatment, the luciferase activities, indicating NFκB activation, were determined in the cells and normalized against the EGFP levels in the same cells. The results thus obtained indicate that, similar to the treatment of Pam3csk4 or inactivated FMDV, treatment of the VLPs induced NFκB activation.

Next, activation of bone marrow derived dendritic cells (BMDCs) by the FMD VLPs were examined as follows. BMDCs were isolated from wild-type or TLR2$^{-/-}$ C57BL/6 mice via routine technology. BMDCs were then stimulated with 1 μg/ml Pam3csk4, 0.1 μm VLPs, or 0.5 μm VLPs for 36 hours at 37° C. Afterwards, the supernatants of the cell cultures were collected and their IL-6 levels were examined by ELISA. The data shows that, like Pam3csk4, VLPs at both doses induced IL-6 secretion in BMDCs from the wild-type mice, but not in BMDCs from the TLR2$^{-/-}$ mice.

The levels of cytokines IL-6, IL-12, and TNF-alpha were examined in BMDCs in the presence or absence of the VLPs (1 μm) 48 hours after treatment. The VLPs were found to stimulate BMDCs to secrete all of these cytokines This result indicates that VLPs activated BMDCs.

Finally, the VLPs were administered to guinea pigs to examine their ability in eliciting antibody responses. Guinea pigs were immunized via intramuscular injection with 100 μg, 200 μg, 300 μg VLPs, or PBS (blank control). Serum samples were collected from the immunized guinea pigs at different time points (0, 1, 2, 3, 4, 5, and 6 weeks after immunization) and the titers of VP1-specific antibodies were examined by ELISA. The results indicate that the titers of anti-VP1 antibodies in guinea pigs immunized with the VLPs were much higher than those in the control animals.

The serum samples mentioned above were inactivated at 56° C. for 30 minutes and then co-incubated with 100 TCID50 viral particles. The serum-virus mixtures were incubated with BHK-21 cells. Forty-eight hours after the incubation, the viral titer in each mixture was examined. Table 2 below lists the dilution fold of each serum sample, at which the 100 TCID50 virus was neutralized by 50%. This dilution fold is reversely proportional to the viral titer in that serum sample.

TABLE 2

| Serum Dilution Folds to Achieve 50% Neutralization | | | | | | | |
|---|---|---|---|---|---|---|---|
| | Weeks | | | | | | |
| | 0 | 1 | 2 | 3 | 4 | 5 | 6 |
| Control | ≤3 | ≤3 | ≤3 | ≤3 | ≤3 | ≤3 | ≤3 |
| VLP (200 μg) | ≤3 | ≤3 | 16 | 256 | 256 | 256 | 256 |
| VLP (300 μg) | ≤3 | ≤3 | 32 | 16 | 16 | 256 | 256 |

The results shown in Table 2 above demonstrate that the VLPs induced neutralizing antibodies that suppressed proliferation of the 100 TCID50 virus.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for producing a capsid protein complex of a picornavirus or a virus-like particle of a picornavirus, said method comprising:

providing an *E. coli* strain containing a plurality of nucleotide sequences, each of which is operably linked to a promoter and contains a first fragment encoding a Smt3 protein and a second fragment encoding a capsid protein of a picornavirus, the first fragment being upstream to the second fragment, wherein the second fragments in all of the nucleotide sequences, taken together, encode all of the capsid proteins for a virus-like particle of the picornavirus, wherein, in at least one of the nucleotide sequences, the first and second fragments are linked via an SfoI restriction site, culturing the *E. coli* strain to allow expression of fusion proteins, each containing Smt3 and one of the capsid proteins, and subsequent formation of capsid protein complexes, wherein each complex is composed of the fusion proteins; and collecting the cells of the *E. coli* strain for isolation of the capsid protein complexes.

2. The method of claim 1, further comprising, after the collecting step, isolating the capsid protein complexes and treating the complexes with an U1p1 protease, thereby producing a virus-like particle composed of the capsid proteins.

3. The method of claim 2, wherein the step of U1P1 protease treatment is performed in the presence of a therapeutic agent and the virus-like particle thus produced encapsulates the therapeutic agent.

4. The method of claim 1, wherein at least one of the nucleotide sequences contains a third fragment encoding a protein tag.

5. The method of claim 4, wherein the third fragment is upstream to the first fragment.

6. The method of claim 4, wherein the protein tag is selected from the group consisting of hexa-His, maltose binding protein, N-utilizing substance A, thioredoxin, calmodulin-binding protein, glutathione S-transferase, and α-factor.

7. The method of claim 1, wherein the *E. coli* strain contains three nucleotide sequences, in which the second fragments encode foot-and-mouth disease virus capsid proteins VP0, VP1, and VP3.

8. The method of claim 7, further comprising, after the collecting step, isolating the capsid protein complexes and treating the complexes with an U1p1 protease, thereby producing a virus-like particle composed of VP0, VP1, and VP3 capsid proteins.

9. The method of claim 8, wherein the step of U1P1 protease treatment is performed in the presence of a therapeutic agent and the virus-like particle thus produced encapsulates the therapeutic agent.

10. The method of claim 7, wherein at least one of the three nucleotide sequences includes a third fragment encoding a protein tag, the third fragment being upstream to the first fragment in the same nucleotide sequence.

11. The method of claim 10, wherein the protein tag is selected from the group consisting of hexa-His, maltose binding protein, N-utilizing substance A, thioredoxin, calmodulin-binding protein, glutathione S-transferase, and α-factor.

12. An *E. coli* cell, comprising a plurality of nucleotide sequences, each of which is operably linked to a promoter and contains a first fragment encoding an Smt3 protein and a second fragment encoding a capsid protein of a picornavirus, the first fragment being upstream to the second fragment, wherein the second fragments in all of the nucleotide sequences, taken together, encode all of the capsid proteins for a virus-like particle of the picornavirus, and wherein, in at least one of the nucleotide sequences, the first and second fragments are linked via an SfoI restriction site.

13. The *E. coli* cell of claim 12, wherein at least one of the nucleotide sequences contains a third fragment encoding a protein tag.

14. The *E. coli* cell of claim 13, wherein the third fragment is upstream to the first fragment in the same nucleotide sequence.

15. The *E. coli* cell of claim 14, wherein the protein tag is selected from the group consisting of hexa-His, maltose binding protein, N-utilizing substance A, thioredoxin, calmodulin-binding protein, glutathione S-transferase, and α-factor.

16. The *E. coli* cell of claim 12, wherein the cell contains three nucleotide sequences, in which the second fragments encode foot-and-mouth disease virus capsid proteins VP0, VP1, and VP3.

17. The *E. coli* cell of claim 16, wherein, in each of the three nucleotide sequences, the first and second fragments are linked via an SfoI restriction site.

18. The *E. coli* cell of claim 16, wherein at least one of the three nucleotide sequences includes a third fragment encoding a protein tag.

19. The *E. coli* cell of claim 18, wherein the third fragment is upstream to the first fragment in the same nucleotide sequence.

20. The *E. coli* cell of claim 18, wherein the protein tag is selected from the group consisting of hexa-His, maltose binding protein, N-utilizing substance A, thioredoxin, calmodulin-binding protein, glutathione S-transferase, and α-factor.

* * * * *